(12) United States Patent
Kato et al.

(10) Patent No.: US 7,311,692 B2
(45) Date of Patent: Dec. 25, 2007

(54) TWO-CHAMBER-TYPE PRE-FILLED SYRINGE

(75) Inventors: Masahiko Kato, Amagasaki (JP); Yasaburo Akagi, Takatsuki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/543,139

(22) PCT Filed: Feb. 18, 2004

(86) PCT No.: PCT/JP2004/001775

§ 371 (c)(1),
(2), (4) Date: Jul. 25, 2005

(87) PCT Pub. No.: WO2004/073774

PCT Pub. Date: Sep. 2, 2004

(65) Prior Publication Data

US 2006/0189943 A1    Aug. 24, 2006

(30) Foreign Application Priority Data

Feb. 19, 2003 (JP) .............................. 2003-040850
Oct. 6, 2003 (JP) .............................. 2003-346718

(51) Int. Cl.
*A61M 37/00* (2006.01)
(52) U.S. Cl. ..................... 604/91; 604/89; 604/90; 604/82; 604/85
(58) Field of Classification Search ........... 604/82–85, 604/89–92, 191, 218, 181, 187, 236
See application file for complete search history.

(56) References Cited

U.S. PATENT DOCUMENTS

| 4,792,329 | A | | 12/1988 | Schreuder | |
|---|---|---|---|---|---|
| 5,665,068 | A | * | 9/1997 | Takamura | ..................... 604/90 |
| 5,935,101 | A | | 8/1999 | Kato et al. | |
| 6,740,060 | B2 | * | 5/2004 | Tanaka et al. | ................. 604/90 |

FOREIGN PATENT DOCUMENTS

| JP | 62-5357 | 1/1987 |
|---|---|---|
| JP | 6-14756 | 4/1994 |
| JP | 10-211280 | 8/1998 |

* cited by examiner

*Primary Examiner*—Kevin C. Sirmons
*Assistant Examiner*—Laura C. Schell
(74) *Attorney, Agent, or Firm*—Wenderoth, Lind & Ponack, L.L.P.

(57) ABSTRACT

A dual-chamber type prefilled syringe comprises a cylindrical body within which a front plug member, a middle plug member and an end plug member are hermetically fitted to form a first chamber and a second chamber. The cylindrical body has an inner surface formed with a bypass. When the middle plug member moves to a position where the bypass is formed, the first chamber is communicated with the second chamber for the first time via the bypass. In this beginning state of liquid transfer (S), an inner volume (VS) of the cylindrical body between a leading end of the cylindrical body and a rear end of the front plug member is set to be at least 60% of a volume (VC) of a second component. When liquid component within the second chamber flows into the first chamber, it is possible to prevent part of the liquid component from passing through the first chamber to reach a portion for attaching an injection needle at a leading end of the cylindrical body.

5 Claims, 6 Drawing Sheets

Fig. 4

COMPARISON TABLE 1: SHOWING BEHAVIOR OF SECOND COMPONENT WHEN CHANGING POSITION FOR ATTACHING FRONT PLUG MEMBER

| | CYLINDRICAL BODY | | STATE BEFORE PREPARING OPERATION FOR ADMINISTRATION | MOVING DISTANCE TO BEGINNING STATE OF LIQUID TRANSFER | | BEGINNING STATE OF LIQUID TRANSFER | | | | LIQUID SPLASHING-OUT PHENOMENON | |
|---|---|---|---|---|---|---|---|---|---|---|---|
| | INNER DIAMETER (mm) | LENGTH (mm) | DISTANCE BETWEEN LEADING END OF CYLINDRICAL BODY AND REAR END OF FRONT PLUG MEMBER (mm) | END PLUG MEMBER (mm) | FRONT PLUG MEMBER (mm) | DISTANCE BETWEEN LEADING END OF CYLINDRICAL BODY AND REAR END OF FRONT PLUG MEMBER (mm) | REFERENCE VOLUME (mL) | VOLUME OF SECOND COMPONENT (mL) | VOLUME RATIO (%) | MOVING SPEED OF END PLUG MEMBER | |
| | | | | | | | | | | 7mm/sec | 20mm/sec |
| EXAMPLE 1 | 10.5 | 95 | 22 | 17 | 12 | 10 | 0.87 | 1.10 | 79 | ◎ | ◎ |
| EXAMPLE 2 | 10.5 | 95 | 27 | 17 | 14 | 13 | 1.13 | 1.10 | 102 | ◎ | ◎ |
| COMPARISON EXAMPLE 1 | 10.5 | 95 | 17 | 17 | 13 | 4 | 0.35 | 1.10 | 31 | ◎ | × |
| EXAMPLE 3 | 10.5 | 90 | 22 | 17 | 14 | 8 | 0.69 | 1.10 | 63 | ◎ | ○ |
| EXAMPLE 4 | 10.5 | 90 | 27 | 17 | 15 | 12 | 1.04 | 1.10 | 94 | ◎ | ◎ |
| COMPARISON EXAMPLE 2 | 10.5 | 90 | 17 | 17 | 12 | 5 | 0.43 | 1.10 | 39 | ◎ | × |
| EXAMPLE 5 | 14.0 | 106 | 22 | 20 | 12 | 10 | 1.54 | 1.65 | 93 | ◎ | ◎ |
| EXAMPLE 6 | 14.0 | 106 | 27 | 20 | 15 | 12 | 1.85 | 1.65 | 112 | ◎ | ◎ |
| COMPARISON EXAMPLE 3 | 14.0 | 106 | 17 | 20 | 16 | 1 | 0.15 | 1.65 | 9 | ◎ | × |

EXPLANATION OF SYMBOLS
◎ : PERCENTAGE OF OCCURRENCE OF LIQUID SPLASHING-OUT  0%
○ : PERCENTAGE OF OCCURRENCE OF LIQUID SPLASHING-OUT  10%
× : PERCENTAGE OF OCCURRENCE OF LIQUID SPLASHING-OUT  AT LEAST 30%

Fig. 5  COMPARISON TABLE 2: SHOWING BEHAVIOR OF SECOND COMPONENT WHEN CHANGING POSITION WHERE BYPASS IS FORMED AND ENTIRE LENGTH OF MIDDLE PLUG MEMBER

| | CYLINDRICAL BODY | | POSITION WHERE BYPASS IS FORMED | MIDDLE PLUG MEMBER | STATE BEFORE PREPARING OPERATION FOR ADMINISTRATION | MOVING DISTANCE TO BEGINNING STATE OF LIQUID TRANSFER | | BEGINNING STATE OF LIQUID TRANSFER | | | | LIQUID SPLASHING-OUT PHENOMENON | |
|---|---|---|---|---|---|---|---|---|---|---|---|---|---|
| | | | | | | | | | | | | MOVING SPEED OF END PLUG MEMBER | |
| | INNER DIAMETER (mm) | LENGTH (mm) | DISTANCE BETWEEN REAR END PORTION AND LEADING END OF CYLINDRICAL BODY (mm) | ENTIRE LENGTH (mm) | DISTANCE BETWEEN LEADING END OF CYLINDRICAL BODY AND REAR END OF FRONT PLUG MEMBER (mm) | END PLUG MEMBER (mm) | FRONT PLUG MEMBER (mm) | DISTANCE BETWEEN LEADING END OF CYLINDRICAL BODY AND REAR END OF FRONT PLUG MEMBER (mm) | REFERENCE VOLUME (mL) | VOLUME OF SECOND COMPONENT (mL) | VOLUME RATIO (%) | 7mm/sec | 20mm/sec |
| EXAMPLE 3 | 10.5 | 90 | 49 | 12.0 | 22 | 17 | 14 | 8 | 0.69 | 1.10 | 63 | ◎ | ○ |
| EXAMPLE 7 | 10.5 | 90 | 52 | 10.5 | 22 | 12 | 9 | 13 | 1.13 | 1.10 | 102 | ◎ | ◎ |
| EXAMPLE 8 | 10.5 | 90 | 54 | 9.0 | 17 | 10 | 4 | 13 | 1.13 | 1.10 | 102 | ◎ | ◎ |
| COMPARISON EXAMPLE 2 | 10.5 | 90 | 49 | 12.0 | 17 | 17 | 12 | 5 | 0.43 | 1.10 | 39 | ◎ | × |

EXPLANATION OF SYMBOLS
◎ : PERCENTAGE OF OCCURRENCE OF LIQUID SPLASHING-OUT  0%
○ : PERCENTAGE OF OCCURRENCE OF LIQUID SPLASHING-OUT  10%
× : PERCENTAGE OF OCCURRENCE OF LIQUID SPLASHING-OUT  AT LEAST 30%

TWO-CHAMBER-TYPE PRE-FILLED SYRINGE

This application is a nationalization of PCT/JP04/01775, filed Feb. 18, 2004.

TECHNICAL FIELD

The present invention concerns a dual-chamber type prefilled syringe comprising a cylindrical body within which a plurality of plug members are hermetically fitted to form a first chamber and a second chamber. Injection medicine, its dissolving solution and its dispersing liquid are preliminarily accommodated within the respective chambers, separately. Upon preparation of administering the medicine to the patient, the first chamber and the second chamber are communicated with each other to be able to disperse and dissolve both of the accommodated components. More particularly, the present invention relates to a dual-chamber type prefilled syringe which inhibits part of a liquid component accommodated in the second chamber from passing through the first chamber to reach a portion for attaching an injection needle which is present at a leading end of the cylindrical body when the liquid component in the second chamber flows into the first chamber on effecting the communication operation as well as the dispersion and dissolution operation.

BACKGROUND ART

For instance, Japanese Patent Public Disclosure No. 62-5357 discloses a conventional example of a dual-chamber type prefilled syringe comprising a cylindrical body provided at a leading end with a portion for attaching an injection needle, within which a first chamber and a second chamber are formed. More specifically, this conventional art, for example as shown in FIG. 6, hermetically fits a front plug member 52, a middle plug member 53 and an end plug member 54 within the cylindrical body 51 in the mentioned order from a leading end side thereof. Formed between the front plug member 52 and the middle plug member 53 is the first chamber 55 which accommodate a first component 56. Further, formed between the middle plug member 53 and the end plug member 54 is the second chamber 57 which accommodates a second liquid component 58. The cylindrical body 51 has an inner surface formed with a bypass 59 in the form of a concaved groove longer than the middle plug member 53, along an axial direction of the cylindrical body 51. When the middle plug member 53 moves toward the leading end side to reach a position where the bypass 59 is formed, the first chamber 55 communicates with the second chamber 57 via this bypass 59. It is noted that an injection needle 61 is attached to the portion 60 for attaching the injection needle at the leading end of the cylindrical body 51 and is covered with a protector cap 62. In addition, a plunger rod 63 is inserted through an opening at a rear end of the cylindrical body 51 and is detachably attached to the end plug member 54.

As for the conventional dual-chamber type prefilled syringe 50, when the end plug member 54 is moved to the leading end side while pressing the plunger rod 63, the middle plug member 53 is pushed and moved through the component 58 accommodated in the second chamber. This enhances an inner pressure of the first chamber 55 to result in moving the front plug member 52. The portion 60 for attaching the injection needle has an interior area provided with a plug accommodation chamber 64 which has an inner peripheral wall formed with concaved communication grooves 65. Thus if the front plug member 52 moves to enter the plug accommodation chamber 64, the first chamber 55 communicates with a liquid passage within the injection needle 61 through the communication grooves 65 and a gap between the front plug member 52 and an inner surface of the plug accommodation chamber 64. In this state, upon further pressing the plunger rod 63, the middle plug member 53 moves to reach the position where the bypass 59 is formed, thereby communicating the first chamber 55 with the second chamber 57 via the bypass 59. In consequence, the pressing of the plunger rod 63 allows the second accommodated component 58 to pass through the bypass 59 and enter the first chamber 55 to result in being mixed with the first accommodated component 56.

However, according to the foregoing conventional technique, at the initial stage of the communication effected between the first chamber 55 and the second chamber 57, the liquid second accommodated component 58 which passes through the bypass 59 possesses so large a kinetic energy that upon pressing excessively quickly the plunger rod 63, the second accommodated component 58 passes through the bypass 59 to vigorously splash out. As a result, part of the splashed out second component reaches the injection-needle attaching portion 60 to cause a likelihood that it flows into the gap between the front plug member 52 within the plug member accommodating chamber 64 and the inner surface of the plug member accommodating chamber 64 as well as into the communication grooves 65.

Once the second accommodated component 58 has entered the communication grooves 65 or the like, it cannot readily return into the first chamber 55. Accordingly, upon pressing the plunge rod 63 thereafter, the second accommodated component is pushed out with the air in the first chamber 55 to leak out of the leading end of the injection needle 61. As a result, the liquid second accommodated component 58 not only dirties or damages the surroundings of the dual-chamber type prefilled syringe 50 but also becomes insufficient in amount to disperse and dissolve the first accommodated component 56 to entail a fear of inappropriately dispersing and dissolving the first accommodated component 56 or the like.

The present invention has a technical object to solve the above-mentioned problems and to provide a dual-chamber type prefilled syringe which prevents part of a liquid component accommodated within a second chamber from passing through a first chamber to reach a portion for attaching an injection needle which is present at a leading end of a cylindrical body when the liquid component flows into the first chamber upon effecting an operation for communicating the first chamber with the second chamber.

DISCLOSURE OF THE INVENTION

In order to accomplish the above object, the present invention has constructed a dual-chamber type prefilled syringe as follows, for example, if we explain it based on FIGS. 1 to 5 that show an embodiment of the present invention.

More specifically, a cylindrical body 2 has a leading end of a first end 2a provided with a portion 3 for attaching an injection needle. Hermetically fitted within this cylindrical body 2 are a front plug member 6, a middle plug member 7 and an end plug member 8 from a side of the first end 2a in the mentioned order. A first chamber 9 is formed between the front plug member 6 and the middle plug member 7, and it accommodates a first component 11. A second chamber 10 is formed between the middle plug member 7 and the end plug member 8, and it accommodates a liquid second component 12. The cylindrical body 2 has an inner surface formed with a bypass 14 in the shape of a concaved groove. This bypass 14 has a length along an axial direction of the cylindrical body 2, which is larger than that of the middle plug member 7. The first chamber 9 and the second chamber 10 are constructed so that they communicate with each other via the bypass 14 when the middle plug member 7 moves toward the first end 2a and arrives at a position where the bypass 14 is formed. An inner volume (VS) of the cylindrical body 2 between the first end 2a of the cylindrical body 2 and a rear end 6b of the front plug member 6 when the middle plug member 7 moves toward the fist end 2a and its rear end 7b has reached a rear end portion 19 of the bypass 14 is set to at least 60% of a volume (VC) of the second accommodated component 12.

The present invention operates as follows.

Upon preparation of administering medicine, the injection-needle attaching portion is directed upwards and then a plunger rod is pressed to move the end plug member toward the first end side. Thus the middle plug member moves toward the first end side and arrives at the position where the bypass is formed, to come to a state where the first chamber and the second chamber communicate with each other for the first time (hereafter called "a beginning state of liquid transfer"). At this time, the movement of the middle plug member enables the first chamber to have its inner pressure increased, so that the front plug member also moves toward the first end side against a frictional force between itself and the inner surface of the cylindrical body.

Upon further pressing the end plug member from the beginning state of liquid transfer, the liquid second component accommodated in the second chamber is transferred into the first chamber via the bypass. When the second accommodated component flows into the first chamber, it results in increasing the inner pressure of the first chamber. In consequence, the front plug member moves toward the injection-needle attaching portion at the first end against the frictional force between itself and the inner surface of the cylindrical body.

At this time, in the event that the end plug member is excessively quickly moved, the second accommodated component vigorously flows into the first chamber and tries to pass through the first chamber. However, since the front plug member is hermetically fitted within the cylindrical body, the second component merely collides against the rear end of the front plug member but it does not reach the injection-needle attaching portion. Although the front plug member moves when the second component has flowed into the first chamber, it moves against the frictional force between itself and the cylindrical body. Therefore, it moves in delay from the flow-in of the second component. The inner volume (hereinafter referred to as 'reference volume') of the cylindrical body between the leading end of the cylindrical body and the rear end of the front plug member in the above-mentioned beginning state of liquid transfer is set to at least 60% of the volume of the second component. Accordingly, the front plug member is positioned within the cylindrical body until the second component has finished its transfer and therefore maintains a sealing state on the leading end side of the cylindrical body.

In the case where the movement of the end plug member is at a lower speed, the front plug member moves with less delay from the flow-in of the second component to the first chamber. In consequence, if the reference volume is set to be smaller than that of the second component, there is caused a case where the front plug member enters, in its entirety, a plug accommodation chamber within the injection-needle attaching portion before the second component finishes its transfer. However, provided that the end plug member is pressed at an appropriate speed or a lower speed than the appropriate speed, the second component flows into the first chamber moderately. Thus there is no likelihood that the second component passes through the first chamber and reaches the injection-needle attaching portion after the front plug member has entered the plug member accommodating chamber in its entirety.

The present invention offers the following advantages.

Even if the end plug member is excessively quickly moved when the second component flows into the first chamber upon communicating the first chamber with the second chamber, the front plug member seals the first end side of the cylindrical body until the second component completes its transfer. For this reason, the second component which has vigorously flowed into the first chamber via the bypass only collides against the rear end of the front plug member and therefore is effectively prevented from reaching the injection-needle attaching portion of the cylindrical body. As a result, it is possible to inhibit the second component from dirtying and damaging the surroundings of the dual-chamber type prefilled syringe and besides to effect a proper dispersion and dissolution of the first component accommodated within the first chamber into the second component that has been transferred into the first chamber.

As the larger reference volume with respect to the volume of the second component can surely seal the leading end side of the cylindrical body even if the front plug member moves in less delay. Thus it is preferably set to at least 75% of the volume of the second component and more preferably set to at least 80%.

In the event that the reference volume is identical to or more than that of the second component accommodated in the second chamber, there is no likelihood that even if the whole second component flows into the first chamber, the front plug member, in its entirety, moves over the leading end of the cylindrical body and enters the plug member accommodation chamber. However, when the reference volume is made larger, there is caused a fear that the cylindrical body becomes unnecessarily longer. Besides, since the front plug member must be pressed through a longer distance, a longer plunger rod is required. This entails a likelihood that it becomes difficult particularly for an operator who has small hands to effect the communication and mixing operation by putting his finger tips on a portion between a flange provided at a rear end portion of the cylindrical body and a rear end of the plunger rod. Further, if the cylindrical body becomes excessively long, the needle's tip is apt to be easily unstable when conducing the administering operation. This results in a fear that the needle's tip that has been pierced into the patient vibrates to give him unnecessary pain.

For the above reason, it is preferable to set the reference volume to be identical to or less than the volume of the second component. Concretely speaking, as for the spacing between the leading end of the cylindrical body in the beginning state of liquid transfer and the rear end of the front plug member, it is preferably not more than 30 mm and more preferably not more than 25 mm.

The bypass must be formed at a position where it does not overlap the middle plug member so as to assure a sealing ability effected by the middle plug member while the cylindrical body is stocked. However, in the case where this bypass is formed at a position as far away as possible from the leading end (first end) of the cylindrical body and has its rear end formed as close as possible to the front end of the middle plug member, it suffices if the middle plug member moves only a small distance to the beginning state of liquid transfer. As a result, it being possible to reduce the distance that the middle plug member moves to the beginning state of liquid transfer, the reference volume can be preferably increased at the beginning state of liquid transfer.

The second component is hermetically accommodated and then sterilized with steam or the like. In order that the first component accommodated within the first chamber thereafter might not be affected by damp, ordinarily two middle plug members are used, one of which is for the first chamber and the other of which is for the second chamber. The entire length of this middle plug member is set to a dimension larger than the inner diameter of the cylindrical body, particularly in the case of a cylindrical body having a small inner diameter, so as to assure sealing ability and to prevent tumbling while being moved. For instance, as for a cylindrical body having an inner diameter of 10.5 mm, two plug members each of which has a length of 6 mm and therefore the middle plug member of 12 mm in total length is used.

On the other hand, in the event that the entire length of the middle plug member is set to be a smaller dimension, for example, 75 to 100% of the inner diameter of the cylindrical body, the bypass can be formed at a position far away from the leading end of the cylindrical body and the middle plug member moves only a short distance to the beginning state of liquid transfer. In consequence, the front plug member also moves a reduced distance to the beginning state of liquid transfer, which results in the possibility of enlarging the reference volume. Thus this is preferable. In addition, in the case of the middle plug member having a small entire length, the middle plug member moves a decreased distance to the beginning state of liquid transfer. Accordingly, it suffices if the first chamber has its inner pressure increased through the movement of the middle plug member by a small amount. Thus even if the first chamber has its volume reduced, it is possible not only to obtain the same effect as in the case of a long middle plug member but also to decrease the entire length of the cylindrical body.

As regards a middle plug member which uses two plug members, if each of the members is made to have the same length, it offers an advantage to facilitate the control of parts. On the other hand, one of the plug member can be formed longer than the other. In this case, the longer plug member preferably supports the shorter plug member. Particularly, the plug member on the side of the first chamber preferably has a length set to a dimension, namely at least 50% of the inner diameter of the cylindrical body so that it might not tumble by the pressure of the liquid passing through the bypass or the like at the time of liquid transfer.

When the middle plug member has its entire length set to a small dimension, even if the bypass has its length reduced, it is possible to transfer the liquid well. And in the case where this bypass has its length reduced, the distance between the leading end of the cylindrical body and the front end portion of the bypass becomes larger to resulting in making it difficult for the second component that has splashed out of the bypass at the time of liquid transfer to reach the leading end of the cylindrical body. Thus this is preferable.

It is possible to elongate the distance between the middle plug member and the leading end of the cylindrical body upon completion of the liquid transfer through forming the bypass at a position far away from the leading end of the cylindrical body and bringing its rear end portion in close contact with the middle plug member or reducing the entire length of the middle plug member. This results in the possibility of enlarging the volume of a space for mixing the first component with the second component when preparing for administration so as to facilitate the mixing operation. Therefore, this is more preferable.

BRIEF DESCRIPTION OF THE DRAWINGS

FIG. 1 is a sectional view showing a dual-chamber type prefilled syringe in a state before a preparing operation for administration. FIG. 2 is a sectional view showing the dual-chamber type prefilled syringe in a state of beginning liquid transfer. FIG. 3 is a sectional view showing the dual-chamber type prefilled syringe when a first component has finished its dispersion and dissolution.

FIGS. 4 and 5 are Comparison Tables which show the measured results of the behavior of a second component. FIG. 4 is a Comparison Table 1 showing the measured results when a front plug member is fitted at varied positions. FIG. 5 is a Comparison Table 2 showing the measured results when changing the position where a bypass is formed and an entire length of a middle plug member.

THE MOST PREFERRED EMBODIMENT OF THE INVENTION

Hereafter, an embodiment of the present invention is explained based on the attached drawings.

Figure 1:
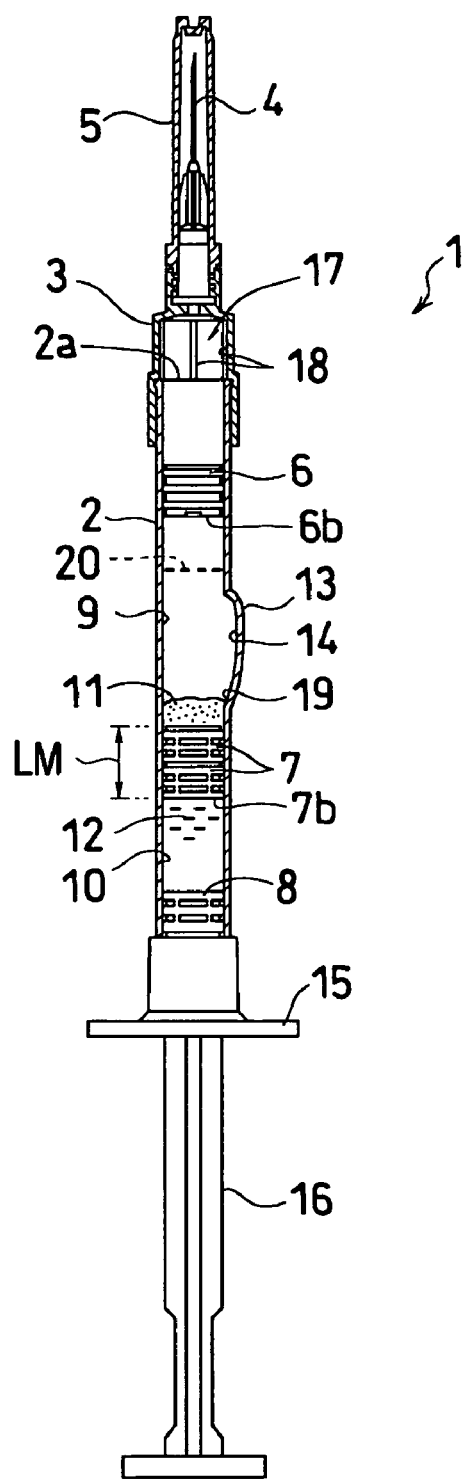
FIGS. 1 to 3 show an embodiment of the present invention.

As shown in FIG. 1, a dual-chamber type prefilled syringe 1 comprises a cylindrical body 2 which has a leading end 2*a* of a first end provided with a portion 3 for attaching an injection needle. An injection needle 4 is attached to the injection-needle attaching portion 3 and is covered with a protector cap 5 in such a manner that the cap 5 covers the injection needle 4.

It is to be noted that according to the present invention, the injection needle 4 may be preliminarily and detachably attached to the injection-needle attaching portion 3 like this embodiment or may be attached thereto after the preparation for administering medicine has been completed.

Hermetically fitted within the cylindrical body 2 are a front plug member 6, a middle plug member 7 and an end plug member 8 in the mentioned order from the leading end side. While a first chamber 9 is formed between the front plug member 6 and the middle plug member 7, a second chamber 10 is formed between the middle plug member 7 and the end plug member 8. The first chamber 9 accommodates a first component 11 such as powdered medicine and the second chamber 10 accommodates a second component 12 such as dissolving solution.

Although this embodiment utilizes powdered medicine for the first component, the first component to be used in the present invention is not limited to that utilized in this embodiment but it may be other solid agents such as freeze-drying agent and may be liquid component. Further, the second component is not limited to the dissolving solution or the dispersing liquid but it may be liquid medicine or the like.

The first chamber 9 has a side wall provided, for example, at a substantially middle portion of the cylindrical body 2, with a projection portion 13 along an axial direction of the cylindrical body 2. This projection portion 13 has an inner surface formed with a bypass 14 in the shape of a concaved groove longer than the middle plug member 7. If this bypass 14 is formed at a position too far away from the leading end 2a of the cylindrical body 2, it results in fitting the middle plug member 7 and the end plug member 8 at positions far away from the leading end 2a of the cylindrical body 2 to cause a problem of increasing the entire length of the cylindrical body 2. However, as for this bypass 14, preferably, it is formed at a position as far away as possible from the leading end 2a of the cylindrical body 2 while its rear end portion 19 is brought into close contact with the middle plug member 7, so long as it does not affect the position for attaching the middle plug member 7 or the like.

The first component 11 is accommodated into the first chamber 9 after the second component 12 has been hermetically accommodated in the second chamber 10 and has been sterilized with steam. The middle plug member 7 is composed of a plug member on the first chamber side and another plug member on the second chamber side in order that the first component might not suffer from an adverse effect because of damp at this time. Needless to say, according to the present invention, the middle plug member 7 may be composed of only one plug member.

As for the middle plug member 7, an employable one has an entire length (LM) larger than an inner diameter of the cylindrical body 2. For example, with the cylindrical body 2 having an inner diameter of 10.5 mm, a plug member of 12 mm in its entire length (LM) may be employed. However, as regards the middle plug member 7, the shorter its entire length, the more preferable, like the dimension of 75 to 100% of the inner diameter of the cylindrical body 2. At this time, in the case where the middle plug member 7 is composed of two plug members, it is preferable to set the length of the plug member on the side of the first chamber 9 to at least 50% of the inner diameter of the cylindrical body 2.

The cylindrical body 2 has a rear end portion provided on an outer surface of the rear end portion with a flange portion 15. The rear end portion of the cylindrical body 2 has an opening through which a plunger rod 16 is inserted. The plunger rod 16 has a leading end fixed to the end plug member 8. When pressing the end plug member 8 through the plunger rod 16, for example, the plunger rod 16 is operated by putting a thumb on the rear end of the plunger rod 16 and placing other finger tips on the flange portion 15.

The plunger rod 16 may be dismantled to make the dual-chamber type prefilled syringe 1 compact while stocking the latter and may be fixed to the end plug member 8 upon preparation of administering medicine.

The injection-needle attaching portion 3 fixed to the leading end of the cylindrical body 2 has an interior area formed with a plug member accommodation chamber 17. This plug member accommodation chamber 17 has an inner peripheral wall provided with concaved communication grooves 18. When the front plug member 6 has been pressed toward the leading end 2a and then has entered the plug accommodation chamber 17, the first chamber 9 is communicated with a liquid passage within the injection needle 4 through these communication grooves 18 as well as through a gap between the front end plug member 6 and an inner surface of the plug member accommodation chamber 17.

Figure 2:
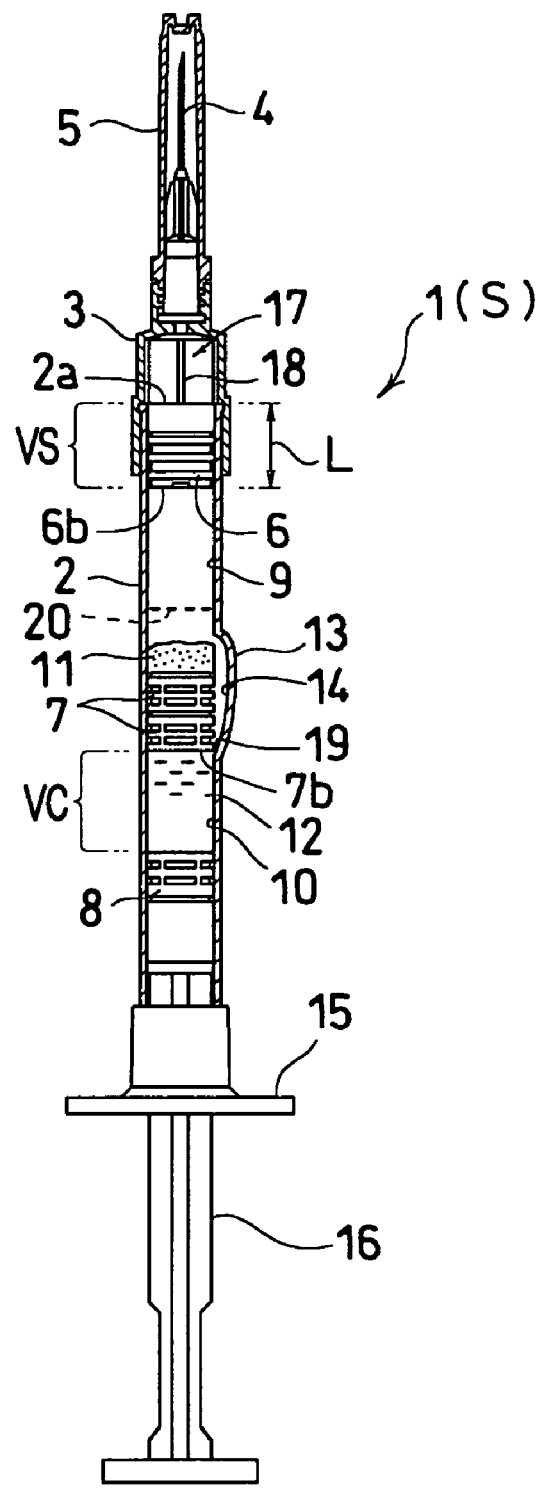

Upon preparation to administer medicine, if the end plug member 8 is pressed through the plunger rod 16, the middle plug member 7 moves and its rear end 7b reaches a rear end portion 19 of the bypass 14, as shown in FIG. 2, to come to a beginning state of liquid transfer (S) where the first chamber 9 is communicated with the second chamber 10 via the bypass 14 for the first time.

At this time, since the first chamber 9 has its inner pressure increased, the front plug member 6 moves toward the leading end 2a. There is produced between the front plug member 6 and the cylindrical body 2 a frictional force which has the front plug member 6 move in delay from the movements of the end plug member 8 and the middle plug member 7.

The moving delay and dimension of the front plug member 6 changes depending on the frictional force. The larger the frictional force, the more the moving delay. Thus the moving dimension is apt to become smaller. This frictional force differs depending on the radial compressibilities of the plug members 6, 7 and 8 when they are fitted to the cylindrical body 2, the contact areas of these plug members to the cylindrical body 2, and the smoothness of the inner surface of the cylindrical body 2 as well as the inner surface treatment thereof. With an excessively large frictional force, there is a fear that the plunger rod 16 cannot be smoothly pushed. On the other hand, with an excessively small frictional force, there is a likelihood that for example, while the plug members 6, 7 and 8 are transported or the like, they are influenced by abrupt changes of the outer pressure and the temperature to inadvertently move. For these reasons, the plug members 6, 7 and 8 have their dimensions arranged so that an adequate frictional force is produced between the inner surface of the cylindrical body 2 and each of the plug members 6, 7 and 8. Further, generally, the inner surface of the cylindrical body 2 is treated with silicon or the like.

In the beginning state of liquid transfer (S), an inner volume of the cylindrical body between the leading end 2a of the cylindrical body 2 and the rear end 6b of the front plug member 6, namely a reference volume (VS) is set to be at least 60% of a volume (VC) of the second component 12, preferably at least 75% and more preferably at least 80%.

The reference volume (VS) is set to a value which is preferably identical to or smaller than the volume (VC) of the second component 12 so that the cylindrical body 2 does not become too much long. Concretely, a spacing (L) between the leading end 2a of the cylindrical body 2 and the rear end 6b of the front plug member 6 is not more than 30 mm and preferably not more than 25 mm.

Upon further pressing the plunger rod 16 from the beginning state of liquid transfer (S) at a position with a tip of the injection needle 4 directed upward, the end plug member 8 moves to flow the second component 12 into the first chamber 19 via the bypass 14. At this time, when operating the movement of the plunger rod 16, for example, at an adequate speed of about 5 to 7 mm/sec. or at a lower speed, the second component which passes through the bypass 14 weakens its vigor to flow into the first chamber moderately. However, if the movement of the plunger rod 16 is operated at an excessively high speed of, for example, about 20 mm/sec., the second component 12 vigorously flows into the first chamber 9 to collide against the rear end 6b of the front plug member 6.

At this time, the front plug member 6 has its rear end 6b positioned within the cylindrical body 2 and besides moves in delay with respect to the flow-in amount of the second component 12. Therefore, the front plug member 6 seals the leading end side of the cylindrical body 2 until the second component 12 finishes its transfer. This results in the possibility of preventing the second component vigorously flowing into the first chamber 9 from passing through the first chamber 9 to reach the injection-needle attaching portion 3.

Figure 3:
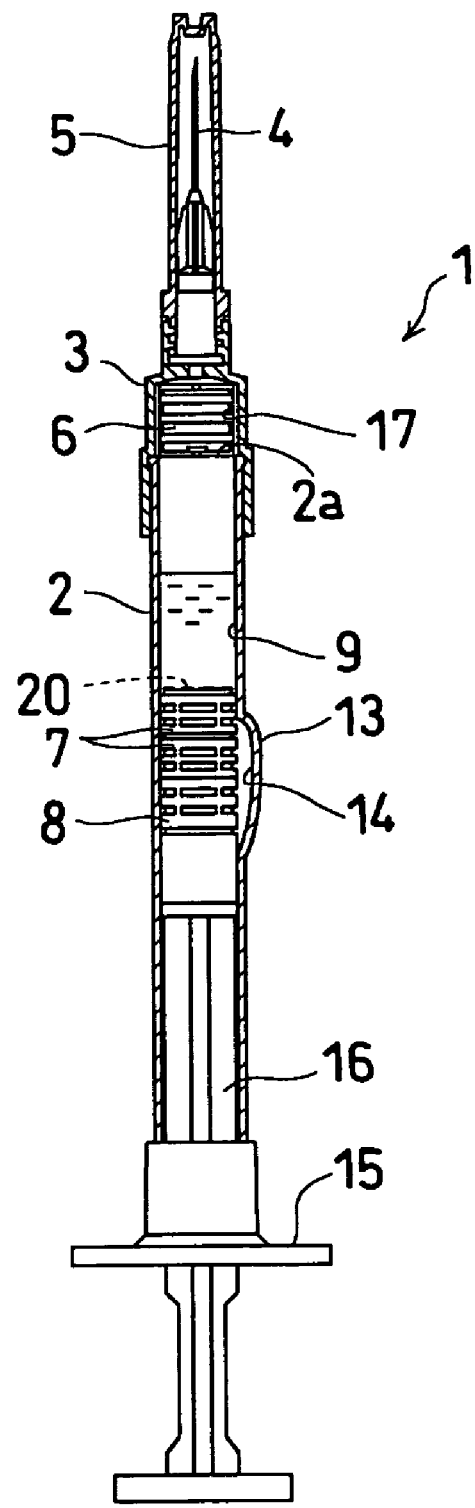
Figure 6:
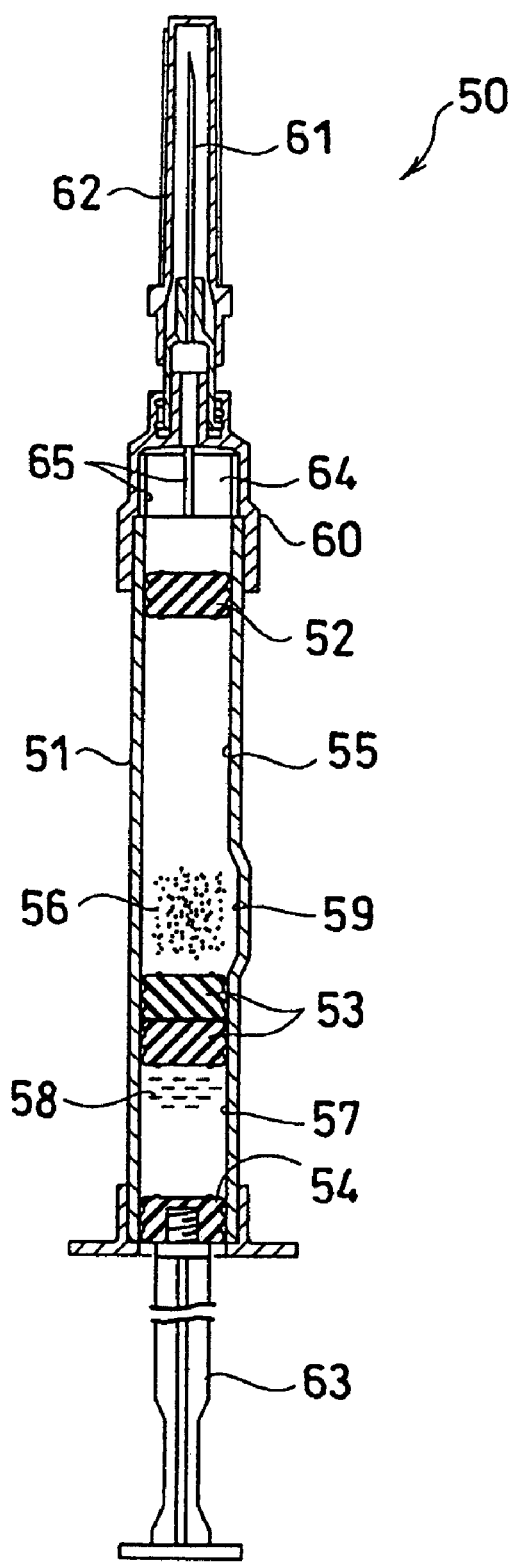
FIG. 6 is a view showing Prior Art and is similar to FIG. 1.

When the end plug member 8 is moved by pressing the plunger rod 16 and is brought into butting contact with the middle plug member 17, the second component 12 completes its transfer. By further pressing the plunger rod 16 from this state where the second component 12 has finished its transfer, as shown in FIG. 3, the middle plug member 17 is made to move until its leading end goes over the leading end portion of the bypass 14 and arrives at an indication line 20 formed at a predetermined position of the cylindrical body 2. At this time, the whole front plug member 6 moves over the leading end 2a of the cylindrical body 2 and has entered the plug member accommodation chamber 17. And after the first component 11 has been dispersed and dissolved in the second component 12, this mixture is deaerated to complete the preparation operation for administering medicine.

Next, with the above-mentioned dual-chamber type prefilled syringe, the behavior of the second component has been measured when the position for attaching the front plug member has been varied. The conditions of every Example and those of the Comparison Examples are as follows.

A first Example utilized a cylindrical body which has an inner diameter of 10.5 mm and has an entire length of 95 mm and employed a front plug member which has a length of 7 mm. And this front plug member was fitted at such a position that its rear end was spaced from a leading end of the cylindrical body at a distance of 22 mm.

A second Example utilized the same cylindrical body and front plug member as those of the first Example. This front plug member was fitted at such a position that its rear end was spaced from a leading end of the cylindrical body at a distance of 27 mm.

A first Comparison Example utilized the same cylindrical body and front plug member as those of the first Example. This front plug member was fitted at such a position that its rear end was spaced from a leading end of the cylindrical body at a distance of 17 mm.

A third Example utilized a cylindrical body which has an inner diameter of 10.5 mm and has an entire length of 90 mm and employed the same front plug member as that of the first Example. This front plug member was fitted at such a position that its rear end was spaced from a leading end of the cylindrical body at a distance of 22 mm.

A fourth Example utilized the same cylindrical body and front plug member as those of the third Example. This front plug member was fitted at such a position that its rear end was spaced from a leading end of the cylindrical body at a distance of 27 mm.

A second Comparison Example utilized the same cylindrical body and front plug member as those of the third Example. This front plug member was fitted at such a position that its rear end was spaced from a leading end of the cylindrical body at a distance of 17 mm.

Further, in the 1st to 4th Examples as well as in the 1st and 2nd Comparison Examples, 1.1 mL of liquid second component was accommodated in the second accommodation chamber.

A fifth Example utilized a cylindrical body which has an inner diameter of 14.0 mm and has an entire length of 106 mm and employed a front plug member which has a length of 7 mm like that of the first Example. This front plug member was fitted at such a position that its rear end was spaced from a leading end of the cylindrical body at a distance of 22 mm.

A sixth Example utilized the same cylindrical body and front plug member as those of the fifth Example. This front plug member was fitted at such a position that its rear end was spaced from a leading end of the cylindrical body at a distance of 27 mm.

A third Comparison Example utilized the same cylindrical body and front plug member as those of the fifth Example. This front plug member was fitted at such a position that its rear end was spaced from a leading end of the cylindrical body at a distance of 17 mm.

In the 5th and 6th Examples as well as in the 3rd Comparison Example, 1.65 mL of liquid second component was accommodated in the second accommodation chamber.

By operating each of the above-mentioned dual-chamber type prefilled syringes, the inner volume of the cylindrical body (reference volume) between the leading end of the cylindrical body and the rear end of the front plug member in the beginning state of liquid transfer was measured. At the same time, the occurrence of the so-called liquid splashing-out phenomenon where the second component reaches the injection-needle attaching portion was measured. These results are shown in Comparison Table 1 of FIG. 4.

Apparently from this Comparison Table 1, in the case where the plunger rod was pressed at an adequate speed of 7 mm/sec, none of the Examples and the Comparison Examples caused the liquid splashing-out phenomenon. However, when the plunger rod was pressed at a higher speed of 20 mm/sec, while the Comparison Examples in which the reference volume is less than 60% of the volume of the second component caused many liquid splashing-out phenomena, the Examples of the present invention in which the reference volume is at least 60% of the volume of the second component seldom caused the liquid splashing-out phenomenon. Particularly, the 1st, 2nd, 4th, 5th and 6th Examples in which the reference volume is set to at least 75% of the volume of the second component caused entirely no liquid splashing-out phenomenon.

Subsequently, with the foregoing dual-chamber type prefilled syringes, as for the behavior that the second component takes when the position for forming the bypass was changed as well as the entire length of the middle plug member, the occurrence of the liquid splashing-out phenomenon was measured as well as the above. The results are shown in the Comparison Table 2 in FIG. 5.

More specifically, in the third Example and the second Comparison Example, the bypass was formed at such a position that its rear end was spaced from the leading end of the cylindrical body at a distance of 49 mm. A plug member of 12 mm in entire length was employed as the middle plug member.

On the other hand, in the seventh Example, the bypass was formed at such a position that its rear end was spaced from the leading end of the cylindrical body at a distance of 52 mm. A plug member of 10.5 mm in entire length was employed as the middle plug member. The other conditions were the same as those of the third Example.

Besides, in the eighth Example, the bypass was formed at such a position that its rear end is spaced from the leading end of the cylindrical body at a distance of 54 mm. A plug member of 9 mm in entire length was employed as the middle plug member. Further, the front plug member was fitted at such a position that its rear end was spaced from the leading end of the cylindrical body at a distance 17 mm like the second Comparison Example. The other conditions were the same as those of the third Example.

Apparently from the comparison of the seventh Example with the third Example, in the case where the bypass is formed at a position far away from the leading end of the cylindrical body and have its rear end brought into close contact with the middle plug member and besides the entire length of the middle plug member is reduced, it suffices if the middle plug member moves only a decreased distance to the beginning state of liquid transfer to result in being able to reduce the moving distance of the front plug member. As a result, the volume ratio can be increased, thereby inhibiting the occurrence of the liquid splashing-out phenomenon even if the plunger rod is pressed at an increased speed of 20 mm/sec.

Additionally, apparently from the comparison of the eighth Example with the second Comparison Example, the third Example or the like, in the event that the bypass is formed at a position further away from the leading end of the cylindrical body and has its rear end brought into close contact with the middle plug member and besides the entire length of the middle plug member is further reduced, it suffice if the middle plug member moves only a more decreased distance to the beginning state of liquid transfer to result in being able to more reduce the moving distance of the front plug member. As a result, the volume ratio can be increased, thereby totally prohibiting the occurrence of the liquid splashing-out phenomenon even if the plunger rod is pressed at an increased speed when the front plug member is fitted near the leading end of the cylindrical body.

INDUSTRIAL AVAILABILITY

The dual-chamber type prefilled syringe according to the present invention comprises a cylindrical body within which a plurality of plug members are fitted to form a first chamber and a second chamber. Injection medicine and its dissolving solution are preliminarily and separately accommodated in the respective chambers. Upon preparation of administering the medicine to the patient, the first chamber is communicated with the second chamber so that both of the accommodated components can be dispersed and dissolved.

The invention claimed is:

1. A dual-chamber type prefilled syringe comprising:
    a cylindrical body which has a first end provided with a portion for attaching an injection needle;
    a front plug member, a middle plug member and an end plug member being hermetically fitted within said cylindrical body in the mentioned order from said first end of said cylindrical body, said front plug member and said middle plug member having rear ends, respectively, on a side away from said first end;
    a first chamber being formed between said front plug member and said middle plug member within said cylindrical body and accommodating a first component;
    a second chamber being formed between said middle plug member and said end plug member within said cylindrical body and accommodating a second component; and
    a bypass formed on an inner surface of said cylindrical body in the shape of a concave groove, said bypass being longer than said middle plug member along an axial direction of said cylindrical body and having a rear end portion on a side away from said first end;
    wherein said first chamber communicates with said second chamber via said bypass when said middle plug member moves toward said first end to reach a position where said bypass is formed; and
    wherein an inner volume of said cylindrical body between said first end of said cylindrical body and said rear end of said front plug member when said rear end of said middle plug member has reached said rear end portion of said bypass is at least 60% of a volume of said second component and not more than said volume of said second component.

2. The dual-chamber type prefilled syringe as set forth in claim 1, wherein a spacing between said first end of said cylindrical body and said rear end of said front plug member when said rear end of said middle plug member has reached said rear end portion of said bypass is not more than 30 mm.

3. The dual-chamber type prefilled syringe as set forth in claim 1, wherein a length of said middle plug member along an axial direction of said cylindrical body is set to a dimension which is 75 to 100% of an inner diameter of said cylindrical body.

4. A dual-chamber type prefilled syringe comprising:
    a cylindrical body which has a first end provided with a portion for attaching an injection needle;
    a front plug member, a middle plug member and an end plug member being hermetically fitted within said cylindrical body in the mentioned order from said first end of said cylindrical body, said front plug member and said middle plug member having rear ends, respectively, on a side away from said first end;
    a first chamber being formed between said front plug member and said middle plug member within said cylindrical body and accommodating a first component;
    a second chamber being formed between said middle plug member and said end plug member within said cylindrical body and accommodating a second component; and
    a bypass formed on an inner surface of said cylindrical body in the shape of a concave groove, said bypass being longer than said middle plug member along an axial direction of said cylindrical body and having a rear end portion on a side away from said first end;
    wherein said first chamber communicates with said second chamber via said bypass when said middle plug member moves toward said first end to reach a position where said bypass is formed;
    wherein an inner volume of said cylindrical body between said first end of said cylindrical body and said rear end of said front plug member when said rear end of said middle plug member has reached said rear end portion of said bypass is at least 60% of a volume of said second component; and
    wherein a spacing between said first end of said cylindrical body and said rear end of said front plug member when said rear end of said middle plug member has reached said rear end portion of said bypass is not more than 30 mm.

5. The dual-chamber type prefilled syringe as set forth in claim 4, wherein a length of said middle plug member along an axial direction of said cylindrical body is set to a dimension which is 75 to 100% of an inner diameter of said cylindrical body.

* * * * *